US006019983A

United States Patent [19]

Van Der Zee et al.

[11] Patent Number: 6,019,983

[45] Date of Patent: Feb. 1, 2000

[54] CARRIER SYSTEM AGAINST GNRH

[75] Inventors: Anna Van Der Zee, Woerden; Irma Marianne Van Die, Gouda; Willem Pieter Martin Hoekstra, Zeist; Josephus Theodorus Gielen, St. Antohonis, all of Netherlands

[73] Assignee: Akzo Nobel N.V., Arnhem, Netherlands

[21] Appl. No.: 08/521,079

[22] Filed: Aug. 29, 1995

Related U.S. Application Data

[63] Continuation of application No. 08/078,661, Jun. 16, 1993, abandoned.

[30] Foreign Application Priority Data

Jun. 19, 1982 [NL] Netherlands ........................ 92.201775

[51] Int. Cl.[7] ........................ A61K 39/02; A61K 39/108; C12P 21/06; C07H 21/04

[52] U.S. Cl. .................................... 424/242.1; 424/180.1; 424/185.1; 424/193.1; 424/195.1; 424/198.1; 424/241.1; 435/69.1; 435/69.4; 435/71.1; 536/22.1; 536/23.1; 536/23.51; 536/23.7

[58] Field of Search .............................. 424/242.1, 257.1, 424/184.1, 185.1, 198.1, 180.1, 193.1, 195.11, 241.1; 435/69.1, 69.3, 69.4, 71.1; 530/300; 536/22.1, 23.1, 23.51, 23.7

[56] References Cited

FOREIGN PATENT DOCUMENTS

| | | | |
|---|---|---|---|
| 0314224 | 5/1989 | European Pat. Off. ..... | A61K 39/108 |
| 2228262 | 8/1990 | United Kingdom ........... | C07K 17/02 |
| 8606635 | 11/1986 | WIPO .......................... | A61K 39/385 |
| WO8606635 | 11/1986 | WIPO . | |
| WO8800056 | 1/1988 | WIPO ............................ | A61K 57/43 |
| WO9003182 | 4/1990 | WIPO ............................ | A61K 37/43 |
| WO9004963 | 5/1990 | WIPO .............................. | A61K 9/50 |
| WO9011298 | 10/1990 | WIPO .............................. | C07K 7/20 |

OTHER PUBLICATIONS

G. Thiry et al., *Applied and Environmental Microbiology*, 55:4:984–993, 1989.

Van Die et al Journal of Bacterology 170:5870–5876, 1988.

Sherwood et al, Neurobiology 80:2794–2798, 1983.

Millar et al, Endocrinology 119:224–231, 1986.

Van Die et al, Mol. Gen. Genet. 222:297–303, 1990 Expression of Foreign Epitopes in P–fimbrial of *E. coli.*

Morrison et al, Research in Veteranary Science 37:108–113, 1984, Adjuvant–Free Immunological Manipulation of Livestock.

Van Die et al Journal of Bacteriology 170:5870 5876, 1988.

Van Die et al Mol. Gen. Genetics 222:297–303 1990.

*Primary Examiner*—Hazel F. Sidberry
*Attorney, Agent, or Firm*—Mary E. Gormley; William M. Blackstone

[57] ABSTRACT

The present invention is concerned with vaccination of mammals against GnRH. The vaccine comprises a GnRH peptide conjugate to *E. coli* fimbrial-filaments and elicits an immune response against GnRH.

6 Claims, 9 Drawing Sheets

FIG. 1

| linker nr | oligonucleotide sequence |
|---|---|
| | BamHI |
| 1: | G CAG CAC TGG AGC TAC GGC CTG CGT CCA GGA TCC CG |
| | gln his trp ser tyr gly leu arg pro gly ser arg |
| | StuI |
| 3: | G CAG CAC TGG AGC TAC GGC CTG AGG CCT GG |
| | gln his trp ser tyr gly leu arg pro gly |
| | BamHI |
| 4: | G ACT CAG CAC TGG AGC TAC GGC CTG CGT CCA GGG GAT CC |
| | thr gln his trp ser tyr gly leu arg pro gly asp pro |
| | BamHI |
| 5: | G GGA TCC CAG CAC TGG AGC TAC GGC CTG CGT CCA GGC GGT CC |
| | gly ser gln his trp ser tyr gly leu arg pro gly gly pro |

FIG. 2

RECOMBINANT HR4 pAI 410 BamHI

GGG | TTG CAG CAC TGG AGC TAC GGC CTG CGT CCA GGA TCC CGA ACC | CTG gly | leu gln his trp ser tyr gly leu arg pro gly ser arg thr | leu pAI 430 StuI

GGG | TTG CAG CAC TGG AGC TAC GGC CTG AGG CCT GGA ACC | CTG gly | leu gln his trp ser tyr gly leu arg pro gly thr | leu pAI 440 BamHI

GGG | TTG ACT CAG CAC TGG AGC TAC GGC CTG CGT CCA GGG GAT CCA ACC | CTG gly | leu thr gln his trp ser tyr gly leu arg pro gly asp pro thr | leu pAI 450
BamHI

GGG | TTG GGA TCC CAG CAC TGG AGC TAC GGC CTG CGT CCA GGC GGT CCA ACC | CTG gly | leu gly ser gln his trp ser tyr gly leu arg pro gly gly pro thr | leu Wild Type

GGG | ACT GCA GGT GAC GCT TAT CCC | CTG gly | thr ala gly asp ala tyr pro | leu

```
                              SEQUENCE LISTING


(1) GENERAL INFORMATION:

   (iii) NUMBER OF SEQUENCES: 30


(2) INFORMATION FOR SEQ ID NO: 1:

     (i) SEQUENCE CHARACTERISTICS:
          (A) LENGTH: 36 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

   (iii) ANTI-SENSE: NO

    (ix) FEATURE:
          (A) NAME/KEY: CDS
          (B) LOCATION: 2..31

    (xi) SEQUENCE DESCRIPTION: SEQ ID NO: 1:

G CAG CAC TGG AGC TAC GGC CTG CGT CCA GGA TCCCG                          36
  Gln His Trp Ser Tyr Gly Leu Arg Pro Gly
    1               5                  10


(2) INFORMATION FOR SEQ ID NO: 2:

     (i) SEQUENCE CHARACTERISTICS:
          (A) LENGTH: 10 amino acids
          (B) TYPE: amino acid
          (D) TOPOLOGY: linear

    (ii) MOLECULE TYPE: protein

    (xi) SEQUENCE DESCRIPTION: SEQ ID NO: 2:
```

-continued

```
Gln His Trp Ser Tyr Gly Leu Arg Pro Gly
  1               5                  10
```

(2) INFORMATION FOR SEQ ID NO: 3:

(i) SEQUENCE CHARACTERISTICS:
(A) LENGTH: 31 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (ix) FEATURE:
(A) NAME/KEY: CDS
(B) LOCATION: 2..31

(ix) FEATURE:
(A) NAME/KEY: misc_difference
(B) LOCATION: replace(31, “”)

(xi) SEQUENCE DESCRIPTION: SEQ ID NO: 3:

```
G CAG CAC TGG AGC TAC GGC CTG AGG CCT GGG                            31
  Gln His Trp Ser Tyr Gly Leu Arg Pro Gly
    1               5                  10
```

(2) INFORMATION FOR SEQ ID NO: 4:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO: 4:

```
Gln His Trp Ser Tyr Gly Leu Arg Pro Gly
  1               5                  10
```

(2) INFORMATION FOR SEQ ID NO: 5:

(i) SEQUENCE CHARACTERISTICS:
(A) LENGTH: 39 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (ix) FEATURE:
(A) NAME/KEY: CDS
(B) LOCATION: 5..34

(xi) SEQUENCE DESCRIPTION: SEQ ID NO: 5:

```
GACT CAG CAC TGG AGC TAC GGC CTG CGT CCA GGG GATCC                   39
     Gln His Trp Ser Tyr Gly Leu Arg Pro Gly
       1               5                  10
```

(2) INFORMATION FOR SEQ ID NO: 6:

(i) SEQUENCE CHARACTERISTICS:
(A) LENGTH: 10 amino acids
(B) TYPE: amino acid
(D) TOPOLOGY: linear -continued (ii) MOLECULE TYPE: protein (xi) SEQUENCE DESCRIPTION: SEQ ID NO: 6:

```
Gln His Trp Ser Tyr Gly Leu Arg Pro Gly
  1               5                  10
```

(2) INFORMATION FOR SEQ ID NO: 7:

(i) SEQUENCE CHARACTERISTICS:
(A) LENGTH: 42 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (ix) FEATURE:
(A) NAME/KEY: CDS
(B) LOCATION: 8..37

(xi) SEQUENCE DESCRIPTION: SEQ ID NO: 7:

```
GGGATCC CAG CAC TGG AGC TAC GGC CTG CGT CCA GGC GGTCC                 42
        Gln His Trp Ser Tyr Gly Leu Arg Pro Gly
          1               5                  10
```

(2) INFORMATION FOR SEQ ID NO: 8:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO: 8:

```
Gln His Trp Ser Tyr Gly Leu Arg Pro Gly
  1               5                  10
```

(2) INFORMATION FOR SEQ ID NO: 9:

(i) SEQUENCE CHARACTERISTICS:
(A) LENGTH: 48 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (ix) FEATURE:
(A) NAME/KEY: CDS
(B) LOCATION: 7..36

(xi) SEQUENCE DESCRIPTION: SEQ ID NO: 9:

```
GGGTTG CAG CAC TGG AGC TAC GGC CTG CGT CCA GGA TCCCGAACCC             46
       Gln His Trp Ser Tyr Gly Leu Arg Pro Gly
         1               5                  10

TG                                                                    48
```

(2) INFORMATION FOR SEQ ID NO: 10:

(i) SEQUENCE CHARACTERISTICS:
(A) LENGTH: 10 amino acids (B) TYPE: amino acid
(D) TOPOLOGY: linear (ii) MOLECULE TYPE: protein (xi) SEQUENCE DESCRIPTION: SEQ ID NO: 10:

```
Gln His Trp Ser Tyr Gly Leu Arg Pro Gly
  1               5                  10
```

(2) INFORMATION FOR SEQ ID NO: 11:

(i) SEQUENCE CHARACTERISTICS:
(A) LENGTH: 42 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (ix) FEATURE:
(A) NAME/KEY: CDS
(B) LOCATION: 7..36

(xi) SEQUENCE DESCRIPTION: SEQ ID NO: 11:

```
GGGTTG CAG CAC TGG AGC TAC GGC CTG AGG CCT GGA ACCCTG                 42
       Gln His Trp Ser Tyr Gly Leu Arg Pro Gly
         1               5                  10
```

(2) INFORMATION FOR SEQ ID NO: 12:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO: 12:

```
Gln His Trp Ser Tyr Gly Leu Arg Pro Gly
  1               5                  10
```

(2) INFORMATION FOR SEQ ID NO: 13:

(i) SEQUENCE CHARACTERISTICS:
(A) LENGTH: 51 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (ix) FEATURE:
(A) NAME/KEY: CDS
(B) LOCATION: 10..39

(xi) SEQUENCE DESCRIPTION: SEQ ID NO: 13:

```
GGGTTGACT CAG CAC TGG AGC TAC GGC CTG CGT CCA GGG GATCCAACCC          49
          Gln His Trp Ser Tyr Gly Leu Arg Pro Gly
            1               5                  10

TG                                                                    51
```

(2) INFORMATION FOR SEQ ID NO: 14:

```
     (i) SEQUENCE CHARACTERISTICS:
          (A) LENGTH: 10 amino acids
          (B) TYPE: amino acid
          (D) TOPOLOGY: linear

    (ii) MOLECULE TYPE: protein

    (xi) SEQUENCE DESCRIPTION: SEQ ID NO: 14:

Gln His Trp Ser Tyr Gly Leu Arg Pro Gly
  1               5                  10


(2) INFORMATION FOR SEQ ID NO: 15:

     (i) SEQUENCE CHARACTERISTICS:
          (A) LENGTH: 54 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

   (iii) ANTI-SENSE: NO

    (ix) FEATURE:
          (A) NAME/KEY: CDS
          (B) LOCATION: 13..42

    (xi) SEQUENCE DESCRIPTION: SEQ ID NO: 15:

GGGTTGGGAT CC CAG CAC TGG AGC TAC GGC CTG CGT CCA GGC GGTCCAACCC      52
              Gln His Trp Ser Tyr Gly Leu Arg Pro Gly
                1               5                  10

TG                                                                    54


(2) INFORMATION FOR SEQ ID NO: 16:

     (i) SEQUENCE CHARACTERISTICS:
          (A) LENGTH: 10 amino acids
          (B) TYPE: amino acid
          (D) TOPOLOGY: linear

    (ii) MOLECULE TYPE: protein

    (xi) SEQUENCE DESCRIPTION: SEQ ID NO: 16:

Gln His Trp Ser Tyr Gly Leu Arg Pro Gly
  1               5                  10


(2) INFORMATION FOR SEQ ID NO: 17:

     (i) SEQUENCE CHARACTERISTICS:
          (A) LENGTH: 27 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

   (iii) ANTI-SENSE: NO

    (ix) FEATURE:
          (A) NAME/KEY: CDS
          (B) LOCATION: 1..27

    (xi) SEQUENCE DESCRIPTION: SEQ ID NO: 17:

GGG ACT GCA GGT GAC GCT TAT CCC CTG                                   27
Gly Thr Ala Gly Asp Ala Tyr Pro Leu
  1               5
```

-continued (2) INFORMATION FOR SEQ ID NO: 18:

(i) SEQUENCE CHARACTERISTICS:
(A) LENGTH: 9 amino acids
(B) TYPE: amino acid
(D) TOPOLOGY: linear (ii) MOLECULE TYPE: protein (xi) SEQUENCE DESCRIPTION: SEQ ID NO: 18:

```
Gly Thr Ala Gly Asp Ala Tyr Pro Leu
  1               5
```

(2) INFORMATION FOR SEQ ID NO: 19:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 19:

```
Gln His Trp Ser Tyr Gly Leu Arg Pro Gly
1               5                   10
```

(2) INFORMATION FOR SEQ ID NO: 20:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 20:

```
CAGCTTTTAA AGGCCTTGGA GCAGCTAAAA                                        30
```

(2) INFORMATION FOR SEQ ID NO: 21:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 21:

```
TTCTTTCGAT GGGTTAACCC TGAAAGATGG                                        30
```

(2) INFORMATION FOR SEQ ID NO: 22:

(i) SEQUENCE CHARACTERISTICS:
(A) LENGTH: 10 amino acids
(B) TYPE: amino acid
(D) TOPOLOGY: linear -continued (ii) MOLECULE TYPE: protein (ix) FEATURE:
(D) OTHER INFORMATION: Glu at position 1 is pyroglutamic acid (xi) SEQUENCE DESCRIPTION: SEQ ID NO: 22:

```
Glu His Trp Ser Tyr Gly Leu Arg Pro Gly
 1               5                   10
```

(2) INFORMATION FOR SEQ ID NO: 23:

(i) SEQUENCE CHARACTERISTICS:
(A) LENGTH: 14 amino acids
(B) TYPE: amino acid
(D) TOPOLOGY: linear (ii) MOLECULE TYPE: protein (xi) SEQUENCE DESCRIPTION: SEQ ID NO: 23:

```
Leu Gln His Trp Ser Tyr Gly Leu Arg Pro Gly Ser Arg Thr
  1               5                   10
```

(2) INFORMATION FOR SEQ ID NO: 24:

(i) SEQUENCE CHARACTERISTICS:
(A) LENGTH: 12 amino acids
(B) TYPE: amino acid
(D) TOPOLOGY: linear (ii) MOLECULE TYPE: protein (xi) SEQUENCE DESCRIPTION: SEQ ID NO: 24:

```
Leu Gln His Trp Ser Tyr Gly Leu Arg Pro Gly Thr
  1               5                   10
```

(2) INFORMATION FOR SEQ ID NO: 25:

(i) SEQUENCE CHARACTERISTICS:
(A) LENGTH: 15 amino acids
(B) TYPE: amino acid
(D) TOPOLOGY: linear (ii) MOLECULE TYPE: protein (xi) SEQUENCE DESCRIPTION: SEQ ID NO: 25:

```
Leu Thr Gln His Trp Ser Tyr Gly Leu Arg Pro Gly Asp Pro Thr
  1               5                   10                  15
```

(2) INFORMATION FOR SEQ ID NO: 26:

(i) SEQUENCE CHARACTERISTICS:
(A) LENGTH: 16 amino acids
(B) TYPE: amino acid
(D) TOPOLOGY: linear (ii) MOLECULE TYPE: protein (xi) SEQUENCE DESCRIPTION: SEQ ID NO: 26:

```
Leu Gly Ser Gln His Trp Ser Tyr Gly Leu Arg Pro Gly Gly Pro Thr
  1               5                   10                  15
```

(2) INFORMATION FOR SEQ ID NO: 27:

(i) SEQUENCE CHARACTERISTICS:
(A) LENGTH: 42 base pairs
(B) TYPE: nucleic acid
(C) STRANDEDNESS: double
(D) TOPOLOGY: linear -continued (ii) MOLECULE TYPE: DNA (genomic)

(iii) HYPOTHETICAL: NO (iii) ANTI-SENSE: NO (xi) SEQUENCE DESCRIPTION: SEQ ID NO: 27:

```
TTGCAGCACT GGAGCTACGG CCTGCGTCCA GGATCCCGAA CC                42
```

(2) INFORMATION FOR SEQ ID NO: 28:

(i) SEQUENCE CHARACTERISTICS:
(A) LENGTH: 36 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 28:

```
TTGCAGCACT GGAGCTACGG CCTGAGGCCT GGAACC                       36
```

(2) INFORMATION FOR SEQ ID NO: 29:

(i) SEQUENCE CHARACTERISTICS:
(A) LENGTH: 45 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 29:

```
TTGACTCAGC ACTGGAGCTA CGGCCTGCGT CCAGGGGATC CAACC             45
```

(2) INFORMATION FOR SEQ ID NO: 30:

(i) SEQUENCE CHARACTERISTICS:
(A) LENGTH: 48 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 30:

```
TTGGGATCCC AGCACTGGAG CTACGGCCTG CGTCCAGGCG GTCCAACC          48
```

CARRIER SYSTEM AGAINST GNRH

This is a continuation of application Ser. No. 08/078,661 filed Jun. 16, 1993, now abandoned.

FIELD OF THE INVENTION

The invention lies in the field of immunology. More specifically the invention is directed at an immunogenic carrier system capable of eliciting an immune response against the "Gonadotropin Releasing Hormone" (GnRH), also referred to as the "Luteinising Hormone Releasing Hormone" LHRH or an analogue or derivative of GnRH.

A recombinant DNA sequence coding for said carrier system, a composition comprising the carrier system and use of said carrier system for immunising a mammal against GnRH also fall within the scope of the invention. The carrier system can for example be comprised in a vaccine or a medicinal preparation.

BACKGROUND OF THE INVENTION

GnRH is a decapeptide with hormonal activity with the following amino acid structure: pGlu-His-Trp-Ser-Tyr-Gly-Leu-Arg-Pro-Gly-$NH_2$ (SEQ ID NO:22), wherein the conventional three-letter code is used and pGlu is pyroglutamic acid and Gly-$NH_2$ is glycine amide. The MRNA of GnRH comprises the GnRH sequence and a signal sequence which is cleaved of after translation followed by cyclization of the N-terminal Gln residue to form pyro-Glu.

It is known that GnRH coupled to a carrier protein can be used to vaccinate mammals. Such a vaccination can be carried out for a variety of reasons, all connected with the natural function of the GnRH. The GnRH formed in the hypothalamus regulates the production and release of the sex hormones LH (i.e. "Luteinising Hormone") and FSH ("Follicle Stimulating Hormone") in the hypophysis. A reduction of the amount of gonadotrophic hormones in the blood results in a reduced stimulation of the gonads, which results in low levels of steroids in blood. A reduction of the blood steroid level to a level comparable to the level obtained after gonadectomy can be realized by effective immunization of the animal against GnRH.

Upon administration of GnRH or its analogue as antigen, i.e. immunogen to a patient or animal, the GnRH or its analogue acts as a vaccine and the host generates antibodies to the GnRH or its analogue which also act against the body's own GnRH. Thus, the analogue's effect will persist after the analogue itself has been metabolised or excreted. This treatment is described for various GnRH analogues or GnRH itself by A. Arimura et al. in Endocrinology 93:1092–1103 (1973); by H. M. Fraser et al. in the Journal of Endocrinology 63:399406 (1974); by S. L. Jeffcoate et al. in Immunochemistry Vol. 11, p. 75–77 (1974); by I. J. Clarke et al. in the Journal of Endocrinology 78:39–47 (1978); by L. Pique et al. in Immunochemistry Vol. 15 pages 55–60 (1978); by V. C. Stevens et al. in the American Journal of Reproductive Immunology 1:307–314 (1981); and in U.S. Pat. No. 3,963,691.

In EP 0,181,236 a description is given of an immunogenic vaccine useful as an effective contraceptive agent, as an agent to treat sexual hyperactivity, for the treatment of cancers and other conditions stimulated by sexual hormones. Said vaccine comprises a conjugate between a carrier protein and one or more nona- and decapeptides derived from GnRH. Said immunisation is reversible which is an advantage over surgical methods.

The International Patent Application WO 88/05308 proposes a method for immunoneutering mammals with a composition comprising an immunogenic protein such as bovine serum albumine, conjugated with a partial peptide of GnRH having a length of 5, 6 or 7 amino acids.

Vaxstrate, the world's first commercially available contraceptive vaccine for cattle, is described as an anti-GnRH two-dose vaccine which has been shown to prevent pregnancy in about 80% of cull cows. Said vaccine comprises use of a synthetic GnRH conjugated to ovalbumin adjuvanted into an oil-based vaccine which then stimulates immunity against GnRH. Such a vaccine should further result in a higher body score and production efficiency.

According to WO 90/11298 a more reliable vaccine than the previously described vaccines can be obtained, that is particularly suited for use in prevention of boar odour of meat. Said vaccine is based on a peptide having a GnRH tandem structure preferably conjugated to a protein such as KLH. Said peptide is initially used in combination with Complete Freund's Adjuvant (CFA), followed by a booster after 8 weeks.

In WO 88/00056 a composition is described comprising two or more different carriers individually coupled to GnRH or analogues of GnRH in amounts sufficient to elicit an immune response against GnRH. Usually a protein carrier and an adjuvant are used and one or more boosters are required.

The known vaccines as described, using GnRH or its analogues after conjugation to protein carriers, are supposed to stimulate the immune system to produce anti-GnRH antibodies which should react with GnRH to effectively reduce its concentration in the body. This technique is however not effective in preventing conception for an initial period of variable length following injection.

In WO 90/03182 a solution for this problem is given by use of a composition comprising (1) free GnRH or its analogue and (2) an immunogenic conjugate between GnRH or its analogue and a carrier protein. Free GnRH or its analogue acts to prevent conception in the mammal during the period from administration to about 6 weeks, until the GnRH antibodies formed in response to the conjugate are metabolised, generally after about 0.5–2 years. The polypeptide conjugates themselves, however, have so far been immunogenically unsatisfactory.

Procedures for the conjugation of GnRH to a polypeptide carrier, e.g. bovine or human serum albumin, or tetanus toxoid or thyroglobulin, have generally involved coupling methods resulting in a poorly defined immunogen unlikely to retain all the structural features of free GnRH in solution as considered desirable from the point of view of obtaining anti-GnRH antibodies capable of blocking functioning of GnRH in vivo. Furthermore there is a danger that the peptide is attached to the carrier through a region important for immunological recognition.

Effective immunisation of mammals using such conjugates to provide a high titer of anti-GnRH antibodies capable of significantly reducing the biological efficacy of endogenous GnRH has indeed only been achieved in the presence of an adjuvant liable to cause undesirable side effects, most commonly Freund's Complete or Incomplete Adjuvant. Freund's Complete Adjuvant interferes with the tuberculin test in cattle. In addition this adjuvant as well as Freund's Incomplete Adjuvant cause a variable amount of chronic inflammatory reaction at the site of injection.

In GB 2,196,969 a vaccine is described comprising analogues of GnRH with a short peptide extension at the C-terminus of the native amino acid sequence which has been predicted by potential energy calculations to have substantially the same conformation as native GnRH in solution and may be readily linked to a polypeptide carrier via the side chain of a cysteine or tyrosine residue provided at the C-terminus.

The vaccines as described generally require large amounts of the vaccine concomitant with severe adjuvants to obtain any antibody response. They have little or no effect on biological activity connected with GnRH. Most of the vaccines described are capable of eliciting an immune response, said immune response merely comprising the formation of antibodies against GnRH and seldom comprising effect on the biological activity of GnRH in a vaccinated mammal. Those vaccines leading to a biological effect do not result in 100% immunisation.

SUMMARY OF THE INVENTION

The subject invention is directed to an immunogenic carrier system capable of eliciting a greatly improved immune response against GnRH or an analogue or a derivative of GnRH. The immune response obtainable from use of a carrier system according to the invention is high enough to affect the biological activity of GnRH in the immunised mammal. In particular the carrier system is suitable for use in effectively suppressing the oestrous cycle, spermatogenesis and/or sexual behaviour of an animal. The carrier system according to the invention can be used in a vaccine, said vaccine no longer requiring such agressive adjuvants as Freunds Adjuvant or Incomplete Freunds Adjuvant to cause an immune response. Less agressive adjuvants can be used.

DETAILED DESCRIPTION OF THE INVENTION

Figure 3:
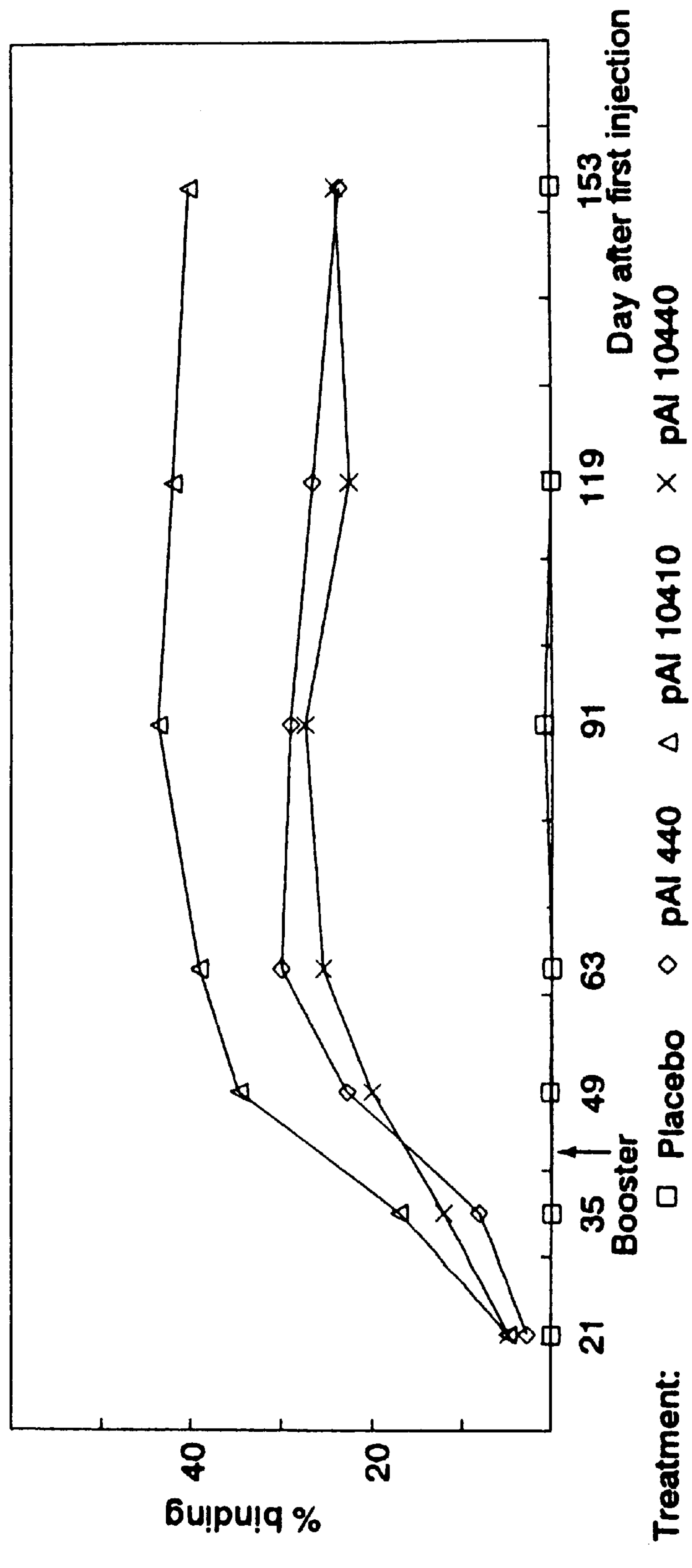

The invention is directed at an immunogenic carrier system capable of eliciting an immune response against GnRH or an analogue or a derivative of GnRH, said carrier system comprising at least a part of an *E. coli* P-fimbrial filament comprising at least a part of major subunit with an insert, said insert comprising a peptide with at least one antigenic determinant for GnRH or an analogue or a derivative of GnRH, said insert being located in the major subunit at a position corresponding to a position in hypervariable region 4 of the wild type major subunit. Wild type in this instance implying the form of the major subunit without the insert.

Fimbrial filaments, also known as fimbriae, are long filamentous appendages that are frequently found in large amounts on many bacterial strains. Each filament is built up of approximately a thousand sub-units that are polymerised in an α-helical way (Korhonen, T. K. and Rhen, M. Am. Clin. Res. 1982, 14, 272–277; Giles, C. L. and Maas, W. K. Prog. Vet. Microbiol. Immuno 1987, 3, 139–158.) Fimbriae structure has been studied in great detail and recombinant fimbrial filaments, also known as hybrid fimbriae, comprising synthetic peptides have previously been described in the literature. A description of the structure of fimbriae and a description of known hybrid fimbriae are given below.

P-fimbriae that are mainly found associated with uropathogenic *Escherichia coli* and are involved in the attachment of the bacteria to epithelial tissue comprise one type of major subunit and several different minor subunits. The localisation and biogenesis of the minor fimbrial components have been studied by Lindberg et al. (Nature (London) 1987 328:84–87 and Riegman et al 1988 Mol. Microbiol. 2: 73–80).

The major subunit of *E. coli* P-fimbriae or P-fimbrillin is predominant and determines the antigenic properties. The serotypes F7–F13 have been alotted to P-fimbriae and said serotypes are known to be specified by the major subunit. Comparison of the amino acid sequences of the major subunit proteins from the various serotypes has revealed five hypervariable regions (HRs) among otherwise more homologous sequences. Said hypervariable regions contain the natural epitopes of the P-fimbriae (van Die et al (1987) Microbiol. Pathogen 3:149–154; van Die et al (1988) FEMS Microbiol. Let. 49: 95–100).

In Mol. Gen. Genet. (1990) 222: 297–303 van Die et al have described how hypervariable regions 1 and 4 (HR1 and HR4) of the major subunit of P-fimbriae with serotype F11 were exploited for insertion of foreign epitopes. Several oligonucleotides coding for antigenic determinants derived from different pathogens were cloned and the resulting recombinant major subunits were sometimes assembled in fimbriae. The assembling of fimbriae only occurred when the length of the inserted peptide did not exceed 14 amino acids.

As already described in the introduction a lot of research has already been carried out on various systems suitable for eliciting an immune response against GnRH. Until now however no experiments with hybrid fimbriae comprising an epitope suitable for eliciting an immune response against GnRH have been described.

GnRH itself is not immunogenic and needs an immunogenic carrier. Due to their polymeric structure fimbriae are highly immunogenic and could possibly act as immunogenic carrier for GnRH or an analogue or derivative of GnRH. Furthermore the inventors presumed that an immunogenic carrier system for a foreign synthetic peptide comprising a P-fimbrial filament with an insert in the major subunit, said insert comprising an antigenic determinant against GnRH, a peptide known to be generally poorly immunogenic could possibly lead to an improved immunogenic response against said synthetic peptide. Furthermore the facts that fimbriated bacteria can be cultivated at low cost and that fimbriae are easily isolated and purified from said bacteria should result in a cheaper and more effective immunogenic carrier system for use in immunising against GnRH.

This could however only be feasible if one of the epitopes of a fimbrial subunit could be replaced without interfering with the formation of the subunit and preferably without interfering with subsequent formation of a fimbrial filament comprising polymerised subunits in large numbers. Furthermore the foreign epitope would have to be present in the fimbrial subunit in a configuration in which the antigenic determinant is suitably exposed for eliciting an immune response and does not interfere with polymerisation of subunits.

Investigations were subsequently carried out by the inventors incorporating a DNA sequence coding for GnRH in the HR1 of a major subunit gene coding for a fimbrial component. Contrary to the results of Van Die et al (1990, Mol. Gen. Genet. 222: 297–303) demonstrating an effective incorporation of peptides other than GnRH in HR1, a microorganism comprising DNA coding for a P-fimbrial filament with an insertion of GnRH in HR1 of the major subunit of a P-fimbrial filament was discovered to be practically incapable of fimbriae formation.

Surprisingly however further investigations by the inventors revealed that a microorganism comprising DNA coding for an *E. coli* P-fimbrial filament with an insertion of a foreign peptide comprising at least one antigenic determinant for GnRH in the HR4 of the major subunit of a fimbrial filament results in good fimbriae formation. More importantly the resulting filaments apparently comprise at least one antigenic determinant for GnRH in a configuration giving good exposure of the determinant. Furthermore an animal injected with a composition comprising such filaments gives an unexpectedly high titer of antibodies against GnRH. In fact the resulting immune response is so high that a biological effect in a process connected with GnRH can be obtained.

The subject invention is therefore directed at an immunogenic carrier system capable of eliciting an immune response against GnRH or an analogue or derivative of GnRH, said carrier system comprising at least a part of an *E. coli* P-fimbrial filament comprising at least a major subunit with an insert, said insert comprising a peptide with at least one antigenic determinant for GnRH or an analogue or derivative of GnRH and said insert being located in the major subunit at a position corresponding to a position in hypervariable region 4 (HR4) of the wild type major subunit.

The peptide with at least one antigenic determinant for GnRH that is comprised in a carrier system according to the invention can be a decapeptide coding for GnRH with the sequence gln-his-trp-ser-tyr-gly-leu-arg-pro-gly (SEQ ID: NO: 19) or a derivative of said sequence comprising at least one antigenic determinant for GnRH. (The amino acid sequence is expressed in the conventional three letter code for amino acids).

The nonapeptide kwsyglrpg is known to elicit an immune response against GnRH (U.S. Pat. No. 4,608,251) as are the partial peptides (with the following single letter amino acid sequences) #ehwsy, #ehwsyg, #ehwsygl, hwsyglr, wsyglr, syglrpg@ and yglrpg@ (WO 88/05308 International Patent Application). Therefore said derivatives are also suitable peptides for comprising a part of a recombinant fimbrial filament of a carrier system for eliciting an immune response against GnRH according to the invention.

Other suitable peptides that can form a component of a carrier system according to the invention are analogues or derivatives of GnRH capable of eliciting an immune response against GnRH. In U.S. Pat. Nos. 3,963,691 and 4,608,251 GnRH analogues are disclosed useful for stimulating anti GnRH antibodies. Therefore a carrier system comprising any analogue described in said patents or any other analogue or derivative of GnRH comprising at least one antigenic determinant capable of eliciting an immune response against GnRH as the peptide incorporated in a part of a major subunit of a P-fimbrial filament is an embodiment of a carrier system according to the invention.

As already stated in this description the serotypes F7 through F13 have been distinguished for P-fimbriae (Orskov, I., and F. Orskov. 1985. *Escherichia coli* in extraintestinal infections. J. Hyg. 95: 551–575). The amino acid sequences of several P-fimbrillins with different serotypes are disclosed in van Die et al., (Microbiol. Pathogen. 3, 149–154, 1987). A carrier system according to the invention can comprise recombinant major subunits derivable from any of the serotypes of the P-fimbriae. In the Examples serotype F11 has been used to illustrate a suitable embodiment of a carrier system according to the invention.

A carrier system as described above comprising a single recombinant major subunit as part of the P-fimbrial filament as well as a carrier system comprising polymerised recombinant major subunits as part of the P-fimbrial filament fall within the scope of the invention.

Preferably the carrier system according to the invention will comprise parts of P-fimbrial filaments or complete P-fimbrial filaments comprising more than one major subunit. A complete recombinant P-fimbrial filament can comprise as many as one thousand recombinant major subunits. The preference for multicopy presence of the peptide capable of eliciting an immune response against GnRH or an analogue or derivative of GnRH in polymerised recombinant major subunits in a carrier system according to the invention stems from the fact that the multicopy presence of an epitope on a fimbrial filament can lead to extremely high immunogenic activity against such an epitope.

A carrier system according to the invention can be obtained through expression of a recombinant DNA sequence coding for at least a part of a P-fimbrial filament comprising at least a major subunit with an insert, said insert comprising a peptide with at least one antigenic determinant for GnRH or an analogue or derivative of GnRH, said insert being located in the major subunit at a position corresponding to a position in hypervariable region 4 (HR4) of the wild type major subunit. Wild type being defined as stated previously in the description. Therefore such a recombinant DNA sequence falls under the scope of the invention.

A recombinant DNA sequence according to the invention comprises at least a DNA sequence L, coding at least for a peptide with at least one antigenic determinant for GnRH or an analogue or derivative of GnRH, with said DNA sequence L being integrated in a DNA sequence S at a position corresponding to a position in the hypervariable region HR4 of the wild type major subunit of a P-fimbrial filament, said sequence S coding for at least a part of the wild type major subunit.

Specific favourable examples of the DNA sequence L in recombinant DNA sequences according to the invention are DNA sequences L comprising DNA coding for the following amino acid sequences:

1) Leu-Gln-His-Trp-Ser-Tyr-Gly-Leu-Arg-Pro-Gly-Ser-Arg-Thr (SEQ ID NO:23);
2) Leu-Gln-His-Trp-Ser-Tyr-Gly-Leu-Arg-Pro-Gly-Thr (SEQ ID NO:24);
3) Leu-Thr-Gln-His-Trp-Ser-Tyr-Gly-Leu-Arg-Pro-Gly-Asp-Pro-Thr (SEQ ID NO:25);
4) Leu-Gly-Ser-Gln-His-Trp-Ser-Tyr-Gly-Leu-Arg-Pro-Gly-Gly-Pro-Thr (SEQ ID NO:26).

Suitable DNA sequences coding for the above-mentioned amino acid sequences in their respective order are given:

1) TTG-CAG-CAC-TGG-AGC-TAC-GGC-CTG-CGT-CCA-GGA-TCC-CGA-ACC (SEQ ID NO:27);
2) TTG-CAG-CAC-TGG-AGC-TAC-GGC-CTG-AGG-CCT-GGA-ACC;
3) TTG-ACT-CAG-CAC-TGG-AGC-TAC-GGC-CTG-CGT-CCA-GGG-GAT-CCA-ACC (SEQ ID NO:29);
4) TTG-GGA-TCC-CAG-CAC-TGG-AGC-TAC-GGC-CTG-CGT-CCA-GGC-GGT-CCA-ACC (SEQ ID NO:30).

A suitable example of a recombinant DNA sequence according to the invention comprises the gene cluster of F11 with DNA sequence L integrated in hypervariable region 4 (HR4) of the major subunit. The genes responsible for synthesis of various serologically different P-fimbriae from uropathogenic *E.coli,* i.e. $F7_1$, $F7_2$, F8, F9, F11, and F13, have been cloned:

De Ree, J. M., P. Schwillens, L. Promes, I. van Die, H. Bergmans, and H. van den Bosch, 1985. Molecular cloning and characterization of F9 fimbriae from a uropathogenic *Escherichia coli.* FEMS Microbiol. Lett. 25:163–169;

De Ree, J. M., P. Schwillens, and J. F. van den Bosch, 1985, Molecular cloning of F11 fimbriae from a uropathogenic *Escherichia coli* and characterization of fimbriae with monoclonal antibodies. FEMS Microbiol. Lett. 29:91–97;

Hacker, J., M. Ott, G. Schmidt, R. Hull, and W. Goebel, 1986, Molecular cloning of the F8 fimbrial antigen from *Escherichia coli.* GEMS Microbiol. Lett. 36: 139–144;

Hull, R. A., R. E. Gill, P. Hsu, B. H. Minshew, and S. Falkow, 1981. Construction and expression of recombinant plasmids encoding type 1 or D-mannose-resistant pili from a urinary tract infection *Escherichia coli* isolate. Infect. Immun. 33: 933–938;

Rhen, M., J. Knowles, M. E. Pentilla, M. Sarvas, and T. K. Korhonen, 1983. P-fimbriae of *Escherichia coli:* molecular cloning of DNA fragments containing the structural genes. FEMS Microbiol. Lett. 19: 119–123;

Van Die, I., G. Spierings, I. van Megen, E. Zuidweg, W. Hoekstra, and H. Bergmans, 1985. Cloning and genetic organization of the gene cluster encoding $F7_1$ fimbriae of a uropathogenic *Escherichia coli* and comparison with the $F7_2$ gene cluster. FEMS Microbiol. Lett. 28: 329–334;

Van Die, I., C. van den Hondel, H.-J. Hamstra, W. Hoekstra, and H. Bergmans, 1983. Studies on the fimbriae of an *Escherichia coli* O6:K2:H1:F7 strain: molecular cloning of a DNA fragment encoding a fimbrial anitgen responsible for mannose-resistant hemagglutination of human erythrocytes. FEMS. Microbiol. Lett. 19: 77–82, and any of these DNA sequences or parts thereof can be used in a recombinant DNA sequence according to the invention.

In some instances it is preferable that the insert, DNA sequence L, of a recombinant DNA sequence according to the invention not only codes for a peptide comprising at least one antigenic determinant for GnRH or an analogue or derivative of GnRH but also comprises DNA coding for further amino acids, flanking the DNA coding for said peptide. DNA sequence L can code for flanking amino acids present at one terminus or at both termini of the peptide comprising at least one antigenic determinant for GnRH or an analogue or derivative of GnRH. Such a flanking amino acid sequence can comprise one or more amino acids. When DNA sequence L comprises such flanking amino acid sequences at both termini of the peptide comprising at least one antigenic determinant for GnRH or an analogue or derivative of GnRH the flanking amino acid sequences can be of equal length and/or of equal composition but may also differ in length and/or composition. The preference for a recombinant DNA sequence comprising a DNA sequence L coding for the presence of a flanking amino acid sequence at one terminus or at both termini of the peptide comprising at least one antigenic determinant for GnRH or an analogue or derivative of GnRH is due to the fact that when said recombinant DNA sequence is expressed a carrier system according to the invention can be obtained in which apparently at least one antigenic determinant against GnRH or an analogue or derivative of GnRH has an improved configuration capable of eliciting a better immune response against GnRH or an analogue or derivative of GnRH than a carrier system in which such flanking amino acid sequences are absent.

A suitable example of such a preferred recombinant DNA sequence according to the invention comprises a DNA sequence L coding for 15 amino acids, wherein the DNA coding for the peptide comprising at least an antigenic determinant for GnRH or an analogue or derivative of GnRH is a decapeptide flanked by two additional amino acids on the N-terminal side and three amino acids on the C-terminal side of said peptide. Another example of such a preferred recombinant DNA sequence according to the invention comprises a DNA sequence L coding for a decapeptide coding for at least one antigenic determinant against GnRH or an analogue or derivative of GnRH flanked on both sides by the coding sequence of one amino acid.

A recombinant DNA sequence according to the invention will preferably comprise a DNA sequence L coding for a peptide with a maximum length of 16 amino acids, as a recombinant microorganism comprising a recombinant DNA sequence according to the invention with an insert coding for more than 16 amino acids is severely restricted in its ability to form recombinant fimbriae.

In a recombinant DNA sequence according to the invention the DNA sequence L can be integrated in DNA sequence S in such a manner that it either completely or partially replaces wild type hypervariable region 4 (HR4).

A recombinant DNA sequence comprising DNA sequence S with DNA sequence L coding at least for a peptide comprising at least one antigenic determinant for GnRH or an analogue or derivative of GnRH integrated in a position corresponding to hypervariable region HR4 of the major subunit, with said DNA sequence S further comprising a mutation in hypervariable region 1 (HR1) and in the adjacent homologous region of the DNA sequence coding for the major subunit is a preferred recombinant DNA sequence according to the invention. This preference is due to the fact that expression of such a recombinant DNA sequence leads to a carrier system according to the invention comprising at least one antigenic determinant of GnRH or an analogue or derivative of GnRH capable of eliciting a better immune response against GnRH or an analogue or derivative of GnRH than an equivalent carrier system according to the invention in which the mutation in HR1 is absent.

A suitable example of such a preferred recombinant DNA sequence comprises a StuI site in the hypervariable region 1 and the adjacent homologous DNA of DNA sequence S coding for at least a part of a major subunit. The mutated DNA sequence in hypervariable region 1 and the adjacent homologous region codes for amino acid sequence Gly-Leu-Gly. Particularly good results were obtained with a recombinant DNA sequence according to the invention wherein the DNA sequence L replacing the HR4 codes for 14 amino acids and wherein a DNA sequence coding for Gly-Leu-Gly replaces nine nucleotides of the DNA sequence coding for the last amino acid of HR1 and the two subsequent amino acids of the adjacent homologous region.

A recombinant DNA sequence according to the invention can also comprise further DNA such as DNA required for various steps in the procedure of biogenesis of fimbrial filaments by a microorganism. Biogenesis of fimbriae includes steps of translocation of the subunits of the fimbriae over the inner membrane of a microorganism, transport of the subunits in the periplasmic space and extrusion of the subunits to the outer membrane with subsequent polymerisation of the subunits into fimbriae.

In the case of a recombinant DNA sequence according to the invention coding for at least a part of a P-fimbrial filament, such further DNA as mentioned in the previous paragraph can comprise one or more of the accessory genes that must be expressed for transportation of subunits and polymerisation of subunits into fimbrial filaments as carried out by a microorganism capable of biogenesis of fimbriae. The accessory genes can be coded by DNA obtained from a microorganism with the same serotype as the microorganism from which the DNA sequence S coding for the subunit can be derived.

The further DNA coding for the accessory genes in a recombinant DNA sequence according to the invention can also be derived from a microorganism with a different serotype of P-filament than the microorganism from which the DNA sequence encoding the recombinant major subunit has been derived due to the fact that the accessory genes derived from DNA coding for different serotypes of P-fimbriae can be exchanged in a microorganism without detrimental effect on the biogenesis of fimbriae.

A further DNA sequence of a recombinant DNA sequence according to the invention can comprise any DNA sequence enabling a microorganism to secrete recombinant major subunit. For example a recombinant DNA sequence according to the invention could comprise a further DNA sequence coding for a signal peptide enabling the recombinant major subunit to pass through the membrane of the microorganism capable of expressing the recombinant DNA according to the invention.

The carrier system according to the invention can be obtained through expression of the above mentioned recombinant DNA sequences from an expression vector. Therefore an expression vector comprising at least a recombinant DNA sequence comprising at least a DNA sequence L coding at least for a peptide with at least one antigenic determinant for GnRH or an analogue or derivative of GnRH with said DNA sequence L being integrated in a DNA sequence S at a position corresponding to a position in the hypervariable region HR4 of the major subunit of a P-fimbrial filament, said sequence S coding for at least a major subunit and an expression vector comprising any of the various embodiments of the recombinant DNA sequence that have been mentioned in the subject description also form part of the invention. Such an expression vector according to the invention can be introduced into a host cell capable of expressing said recombinant DNA sequence in a manner well known to the expert e.g. by transformation of a microorganism.

A host cell comprising at least a recombinant DNA sequence comprising at least a DNA sequence L coding at least for a peptide with at least one antigenic determinant for GnRH or an analogue or derivative of GnRH with said DNA sequence L being integrated in a DNA sequence S at a position corresponding to a position in the hypervariable region HR4 of the major subunit of a P-fimbrial filament said sequence S coding for at least a major subunit and a host cell comprising any of the embodiments of a recombinant DNA sequence as given in the subject description also fall under the scope of the invention. The host cell can comprise said recombinant DNA sequence on an expression vector or integrated in its chromosome. The host cell will preferably be a micro organism such as a bacterial cell.

A host cell comprising the recombinant DNA sequence is preferably capable of biogenesis of fimbriae. Biogenesis of fimbriae includes steps of translocation of the subunits of the fimbriae over the inner membrane of the host cell, transport of the subunits in the periplasmic space and the extrusion of the subunits to the outer membrane with subsequent polymerisation of the subunits.

A host cell comprising a recombinant DNA sequence according to the invention, the recombinant host cell being incapable of biogenesis of recombinant fimbriae also falls under the scope of the invention. Such a fimbriae-recombinant microorganism can comprise DNA enabling the microorganism to secrete recombinant major subunits or parts thereof into the culture medium of said recombinant microorganism. In such a recombinant microorganism the recombinant major subunits of the recombinant P-fimbrial filament can be transported to the periplasmic space without the subsequent polymerisation or transfer over the outer membrane to form recombinant P-fimbrial filaments comprising polymerised major subunits. In such a case the single recombinant major subunits comprising peptide comprising antigenic determinant for GnRH or an analogue or derivative of GnRH can be obtained from the microorganism in a manner well known to the expert.

As already previously stated in the description a preferred carrier system according to the invention comprises polymerised recombinant subunits. A simple method for obtaining a carrier system according to the invention comprising polymerised subunits involves expression of a recombinant DNA sequence according to the invention by a microorganism capable of expressing said recombinant DNA, said microorganism also being capable of polymerisation of the resulting recombinant subunits. Said polymerisation can take place during transfer of the subunits through the outer membrane as a step in biogenesis of fimbriae.

The resulting recombinant fimbriae can be easily isolated from such a recombinant microorganism. Such isolation shall preferably be carried out in non-denaturing circumstances in order to maintain the structure of the recombinant fimbrial filament. Riegman, N. et al describe a method for obtaining purified fimbriae in J. Bacteriol. 1990 172:1114–1120.

Preferably the recombinant microorganism will be easily discerned from the non-recombinant microorganism. This can be achieved by use of a microorganism that is incapable of biogenesis of fimbriae or by use of a microorganism that is incapable of producing fimbriae with a distinctive characteristic of the recombinant fimbriae. Any fimbriae$^-$ microorganism can be used as expression vehicle for recombinant DNA according to the invention.

Bacteria carrying P-fimbriae (usually found on uropathogenic *Escherichia coli*) bind to the α-D-gal(1→4)β-D-gal moiety of P-blood group antigens. It is therefore simple to detect bacteria carrying P-fimbriae as said fimbriae will adhere to human erythrocytes in the presence of mannose which can be easily visualised as agglutination of the erythrocytes. A microorganism that cannot adhere to human erythrocytes before introduction of recombinant DNA according to the invention can be used as the expression vehicle for recombinant fimbrial filaments of the P-type. The resulting recombinant microorganism will be capable of adhesion to human erythrocytes in contrast to the original microorganism.

A suitable example of an expression vehicle for recombinant DNA according to the invention is the *E. coli* K12 strain HB101 (Boyer H. W., Roulland-Dussoix D (1969) J.Mol.Biol. 41: 459–472). Until recently it was believed that HB101 is deficient in the production of type 1 fimbriae, however in Microbial Pathogenesis (1991) 10, 481–486 Elliott, S. J. et al describe that a standing culture of HB101 was able to develop type 1 fimbriae. To be certain the developing fimbriae are in fact recombinant fimbriae derived from expression of recombinant DNA the HB101 cells should be grown in solid media or in broth media with agitation.

Another example of an *E. coli* K12 strain that does not produce type 1 fimbriae is AM1727, a recA derivative of JE2571 (van Die et al (1983) FEMS Microbiol.Let. 19, 77–82). A further example of a useful microorganism for producing recombinant fimbriae for a carrier system according to the invention is JA221 (Clark L; and Carbon J. (1978) J.Mol.Biol. 120:517–532).

DNA that must be expressed in order to enable biogenesis of recombinant fimbrial filament can either be partially available in the non-transformed microorganism or can be completely comprised on the recombinant DNA sequence according to the invention that is introduced into said microorganism. The DNA enabling the biogenesis can be introduced as part of the recombinant DNA sequence according to the invention but can also be comprised on a separate expression vector.

In the Examples a description is given for obtaining various carrier systems according to the invention through preparation of several recombinant DNA sequences according to the invention and transformation of said sequences to fimbriae-deficient microorganisms from which the resulting recombinant fimbrial filaments can be isolated and purified. The recombinant DNA, the microorganisms comprising said recombinant DNA and compositions comprising a carrier system as described in the Examples also fall within the scope of the invention.

The invention is also directed at a composition suitable for eliciting an immune response against GnRH or an analogue or derivative of GnRH, said composition comprising a carrier system as described in the subject description. A composition suitable for eliciting an immune response against GnRH or an analogue or derivative of GnRH comprising the expression product obtainable from a recombinant DNA sequence according to the invention, for example from a microorganism as described above, also falls under the scope of the invention.

The invention is furthermore directed at use of such a composition for producing an immune response against GnRH or an analogue or derivative of GnRH. In particular at the use of such a composition in an amount and a manner that are sufficient to affect the biological activity of GnRH in an animal. A composition according to the invention is especially suited for use in suppressing the oestrous cycle, spermatogenesis and/or sexual behaviour of an animal sufficiently to prevent conception. Preferably a composition comprising a carrier system derived from a microorganism that was capable of biogenesis of P-fimbriae is used. The composition according to the invention can be used in a vaccine or any medicinal preparation suitable for eliciting an immune response to GnRH or an analogue or derivative of GnRH.

In fact a composition according to the invention can be used for any of the applications described in the state of the art for the various known compositions, vaccines and medicinal preparations comprising antigenic determinants for GnRH or an analogue or derivative of GnRH. The examples of numerous possible applications that have been given in the introductory part of the subject description therefore serve as examples of various uses of a composition according to the invention.

The composition according to the invention can be applied without the use of strong adjuvants such as Freunds Adjuvant and Incomplete Freunds Adjuvant, enabling the use of such a composition according to the invention in immunisation of animals including mammals without the concomitant negative effects of the mentioned adjuvants. Suitable adjuvants include for example aluminium salts (for example $Al(OH)_3$, AlPO4, $Al_2(SO_4)_3$), oil-in-water emulsions (Bayol F$^{(R)}$, Marcol F$^{(R)}$), vitamin-E acetate solubilisate or saponins, if desired one or more emulsifiers such as Tween$^{(R)}$, Span$^{(R)}$ are also incorporated into the vaccine.

Above all use of such a composition according to the invention in immunisation of animals including mammals not only leads to the development of antibodies against GnRH or an analogue or derivative of GnRH, but in fact leads to altered biological activity due to neutralisation of GnRH by the antibodies elicited by use of such a composition. In particular the use of a composition according to the invention leads to suppression of reproductive activities in an animal on which said composition has been used.

The composition according to the invention can be applied in the form of a vaccine. The vaccine can be applied subcutaneously or intramuscularly in a mammal that is to be immunised in a manner well known to the expert. Preferably one or more booster injections are given. Each injection will contain 0.01–1 mg of GnRH-antigen or GnRH-analogue-antigen or GnRH-derivative-antigen.

In Examples 3 and 4 the use of a composition according to the invention for immunizing animals are further illustrated.

EXAMPLE 1

In this example a description is given of insertion of genetic information coding for GnRH in the gene encoding the major subunit of P-fimbriae with serotype F11.

A) Preparation of Recombinant DNA

Plasmid pPIL291-15 deposited at the CNCM of the Institut Pasteur under number I-709 was used to construct the plasmids pPIL291-1510 and pPIL291-1519. Plasmid pPIL291-15 comprises the genetic organisation of the F11 gene cluster. The BamHI-Cla1 fragment of pPIL291-15 comprises the gene coding for the F11 major subunit, the FelA gene.

The construction of plasmids pPIL291-1510 and pPIL291-1519 was carried out as described in Van Die et al, Mol. Gen. Genet (1990) 222:297–303 and Van Die et al (1988) J. Bacteriol. 170: 5870–5876.

The 0.7 kb HindIII-EcoRI fragment of pPIL291-151 (obtained from cloning the 3kb ClaI-BamHI fragment of PPIL 291-15) was cloned into the bacterial phage vector m13mp8. This clone was used as a template for site directed mutagenesis.

Site directed mutagenesis was performed by the gapped duplex method (Kramer V. et al (1984) Nucl. Acid Res. 12:9441–9456) essentially as described before (Van Die, I. et al (1988) J. Bacteriol. 170:5870–5876).

The obtained double stranded DNA molecule was transformed to strain HB2154, white plaques were selected and restriction fragment DNA was isolated and checked.

The mutagenic primer for HR1 had the following nucleotide sequence CAGCTTTTAAAGGCCTTGGAG-CAGCTAAAA (SEQ ID NO: 20). In the mutagenesis experiment the bases 355–362 of the wild type F11 sequence were replaced by different bases resulting in the modification of three amino acids in this region leading to the introduction of the StuI restriction site (AGGCCT) in the resulting DNA molecule.

The mutagenic primer for HR4 had the following nucleotide sequence TTCTTTCGATGGGTTAACCCTGAAA-GATGG (SEQ ID NO: 21). In the mutagenesis experiment bases 502–520 of the wild type F11 sequence were replaced by four new bases resulting in a deletion of 15 bases and the presence of a HpaI restriction site (GTTAAC) in the resulting DNA molecule.

The HindIII-EcoRI fragments were subsequently isolated and were used to replace the EcoRI-HindIII fragment of plasmid pPIL291-151 resulting in the respective plasmids pPIL291-1510 (comprising a StuI restriction site in the hypervariable region 1 HR1) and pPIL291-1519 (comprising a restriction site for HpaI in the hypervariable region 4 HR4). Both cloning sites were constructed in the same reading frame.

Several oligonucleotides of varying lengths were inserted into pPIL291-1510 and/or pPIL291-1519. The inserted oligonucleotides all code for the decapeptide GnRH with amino acid sequence gln his trp ser tyr gly leu arg pro gly. The oligonucleotides differ with respect to the length and the composition of amino acid sequences flanking the decapeptide.

FIG. 1 and SEQ ID NO: 1–8: show the oligonuclotides that were inserted into plasmids pPIL291-1510 and pPIL291-1519. The coding strand of GnRH translated into the corresponding amino acids is underlined.

After isolation of transformed cells comprising plasmids the plasmids containing inserts with linkers 1 (SEQ ID NO:1, 2), 4 (SEQ ID NO: 5, 6) and 5 (SEQ ID NO: 7, 8) were selected by determination of the presence of a site for restriction endonuclease BamHI.

For detecting a plasmid comprising linker 3 (SEQ ID NO: 3, 4) as insert the StuI recognition site in the oligonuclotide could not be used as the StuI recognition site was immediately followed by two guanidine nucleotides forming a site that is recognised by *E. coli* methylase and is therefore protected from restriction because of methylated cytidine residues. For selection of incorporation of linker 3 the plasmids were therefore digested with StuI for detecting an insertion in HR1 and were digested with HpaI for detecting an insertion in HR4. Successful incorporation of an oligonuclotide in the respective hypervariable regions HR1 and HR4 resulted in removal of the corresponding restriction sites.

Subsequently the selected plasmids were sequenced in order to determine the presence of the linker in the correct orientation. The plasmids obtained as described with linkers in the desired orientation were designated pAI X.Y.0, whereby X indicates the presence of the hypervariable region, Y indicates the presence of the inserted linker and 0 indicates the presence of the accessory genes.

The plasmids derived from pPIL291-1510 were therefore denoted as pAI 110, pAI 130, pAI 140, pAI 150. In recombinant hypervariable region 1 HR1 i.e. after insertion into plasmid pPIL291-1510, the oligonucleotides are preceded by a codon for a glycine residue.

The plasmids obtained from pPIL291-1519 comprising the linkers demonstrated in SEQ ID NO: 1–8 were denoted pAI 410 (SEQ ID NO: 9, 10), pAI 430 (SEQ ID NO: 11,12), pAI 440 (SEQ ID NO: 13, 14) and pAI 450 (SEQ ID NO: 15, 16) respectively. The oligonucleotides inserted into hypervariable region 4 HR4 of plasmid pPIL291-1519 are preceded in the recombinant hypervariable region HR4 by a leucine residue. The last amino acid of the recombinant hypervariable region 4 is a threonine.

In FIG. 2 and SEQ ID NO: 9–16 the DNA sequences and corresponding amino acid sequences of the recombinant hypervariable region 4 HR4 of the plasmids pAI 410 (SEQ ID NO: 9, 10), 430 (SEQ ID NO: 11, 12), 440 (SEQ ID NO: 13, 14) and 450 (SEQ ID NO: 15, 16) are given as well as the DNA sequence and the amino acid sequence of the wild type HR4 of F11 (SEQ ID NO: 17). The coding regions of GnRH translated in according amino acids are indicated in the respective information chapters of the sequence listing under (ix) feature (B) location.

In Table I a comparison is given of the flanking sequences of the decapeptide GnRH coding for at least one antigenic determinant for GnRH as well as a comparison of the lengths of the recombinant hypervariable region 4 HR4 and the wild type hypervariable region 4 HR4.

B) Analyses of Fimbriae Obtained from Expression of the Recombinant DNA

The ClaI/BamHI restriction fragment, harbouring the FelA gene, of pPIL291-15 was replaced by the mutated ClaI-BamHI fragments of the pAI-plasmids containing the linkers 1, 3, 4 and 5 respectively and the resulting four plasmids were transformed to competent cells of HB101.

Haemagglutination positive clones were selected and checked by DNA restriction fragment analysis. Expression of the hybrid fimbriae by the transformed HB101 cells was also examined by electron microscopy. The results are summarised in Table 2.

From these tests it was suggested that HB101/PAI 440 expressed fimbriae nearly as efficiently as HB101/pPIL291-15 carrying the normal F11-gene cluster. Fimbriae production was only slightly reduced in HB101 cells harbouring plasmids pAI 410 and 430. The insertion of linkers in hypervariable region 1 appeared to severely disturb the biogenesis of the fimbriae as only a few fimbriae per cell could be detected.

The expression of recombinant fimbriae was also examined through an ELISA assay with polyclonal antibodies placed against the complete bacteria comprising wild-type F11 fimbriae. This was carried out as the use of monoclonal antibodies was impossible due to distortion of the F11 specific epitopes through the new ligations (a phenomenon described in Van Die et al MGG222 (1990) blz. 297–303). The results are given in Table 3.

Materials and Methods.

a) Bacteria

*Escherichia coli* strain HB101 deficient in type 1 fimbriae formation was used as the host strain for morphogenetic expression of hybrid fimbriae (Boyer, H. W., and D. Roullard-Dussoix (1969); J. Mol. Biol. 41: 459–472) HB101 was cultured on a rotary shaker to ensure that the non transformed cells were fimbriae$^-$.

For DNA sequencing strain JM101 was used as the host for M13MP8 derivatives (Messing, J., and J. Vieira (1982); Gene 19: 269–276).

In site directed mutagenesis experiments HB2154 was used as the host strain for M13mp18 derivatives (Carter, P., H. Bedouelle, and G. Winter (1985); Nucl.Acids Res. 13: 4431–43).

Bacteria were grown on Brain Heart Infusion broth containing ampicillin (50 $\mu$g/ml).

b) Enzymes

Restriction endonucleases were used according to instructions of the manufacturer.

For ligation T4 DNA ligase was used according to instructions of the manufacturer.

c) DNA Analyses

Analysis of DNA fragments was performed by electrophoresis in 0.6% agarose gels.

In DNA sequencing the dideoxy chain termination method of Sanger et al (Sanger, F., S. Nicklen, A. R. Coulson (1977); Proc. Natl. Acad. Sci. USA 74: 5463–67) was used.

d) Transformations

Transformations were carried out according to Kushner (Kushner, S. R. (1978); p. 17–23 In: H. W. Boyer and S. Nicosia (ed) Genetic Engineering. Elsevier Biomedical Press, Amsterdam).

e) Localised Mutagenesis

Localised mutagenesis was performed by the gapped duplex method. The primer was hybridised with template DNA together with M13mp18 for one hour at 65° C. Extension and ligation of this gapped duplex molecule was performed after addition of the required dNTP's, 10 units of T4 ligase and 3 units of Klenow fragment of DNA polymerase I followed by a 4 hour incubation at 16° C.

f) Linker Synthesis

The GnRH oligonucleotides were synthesised using a DNA synthesizer model 381A of Applied Biosystems as is explained in the Users Manual.

g) Insertion of Linkers

Plasmid pPIL291-1519 was digested with HpaI in the following manner: A mixture was prepared of 1 μg DNA, 5 units of restriction enzyme HpaI, 1.5 μl of a restriction buffer (10×) made up to 15 μl with TE buffer (10 mM tris 1 mM EDTA) and this mixture was incubated at 37° C. for 1½ hours. The enzyme was subsequently inactivated by heating at 65° C. for 10 minutes and the mixture was subjected to a phenol extraction followed by alcohol precipitation.

The linearised plasmid was ligated with GnRH linker in the following manner:

A mixture was prepared of 5 units ligase, 1 μl ligase buffer (10×), vector DNA and linker DNA in a volume of 10 μl. The ligation was carried out O/N at 16° C.

Transformation was carried out by mixing 100 μl of competent cells (Kushner, S. R. (1978); p. 17–23 In: H. W. Boyer and S. Nicosia (ed) Genetic Engeneering. Elsevier Biomedical Press, Amsterdam) of HB101 with the ligated plasmid for 30 minutes on ice. This mixture was subsequently subjected to a heatshock for 5 minutes at 37° C. LB-medium was added and after 1½ hours was plated out on Amp plates. The resulting colonies were isolated, cultivated and the plasmid DNA was isolated and sequenced from these colonies.

The same procedure was followed for GnRH insertion in HR1 with the exception of digestion with StuI instead of HpaI.

h) Complete Bacteria ELISA

The antiserum that was used was an absorbed hyperimmune rabbit antiserum raised against F11 fimbriae.

In each assay a positive and a negative control strain were included.

After washing the bacteria were seeded in flat bottom polystyrene microtiter plates. The bacterial suspensions were allowed to dry and after washing they were blocked with PBS/Tween-80/Newborn Calf Serum. Subsequently serial dilutions of absorbed serum were added and after 1 h incubation at 37° C. the plates were washed and peroxidase-conjugated goat-anti-rabbit IgG(H+L) was added. After washing and adding of TMB-substrate buffer, containing ureum-peroxide and 3,3',5,5'-tetramethylbenzidine the reaction was stopped by adding $H_2SO_4$ and colouring was measured with a Microelisa reader. Titers were determined as the highest antiserum dilution giving an $A_{450}$ of at least 2 times the background $A_{450}$.

i) Production, Isolation and Purification of Hybrid GnRH-F11 fimbriae

*E.Coli* K-12 strains, transformed with plasmids pAI 410, pAI 440, pAI 10410 and pAI 10440 and maintained at −70° C. in 30% glycerol, were passed through two pre-cultures (overnight at 37° C. on plates with Blood Agar Base no.2 (Oxoid)+100 μg/ml ampicillin and for 7 hours at 37° C. in 100 ml Brain Hearth Infusion medium (BHI, Oxoid)+ ampicillin (100 μg/ml) with agitation).

For main-culture a fermentor, filled with 12 liter BHI, ampicillin (100 μg/ml) and 5 ml 10% PPG (antifoam), was inoculated with the preculture and grown for 17 hours (37° C.; 50% $O_2$ saturation, adjusted with air; agitation 100–1000 rpm).

The fimbriae were removed from the cultured bacteria by heating at 65° C. (15 min), treatment at pH10 (1h, room temp., agitation) and centrifugation (15 min, 13000 rpm Sorvall RC-5B, rotor GSA).

After concentration of the supernatant to 200–600 ml (XM 300 filter, Minitan System, Millipore) and washing with Tris/Glycine buffer (pH 10), the pH was adjusted to 8.5 and the resulting precipitate was allowed to settle for at least 1 day at 4° C.

After harvesting the precipitate (20 min centrifugation at 48,000 g, 4° C.) the pellet was dissolved in 100 ml Tris/Glycine buffer pH 8.5 with 2 M urea. This preparation was concentrated (YM100 filter, Amicon ultrafiltration cell), washed (2×200 ml Tris/Glycine buffer pH 8.5) and stored at −20° C. until used for vaccin production.

EXAMPLE 2

A mutation in hypervariable region 1 and an insertion in hypervariable region 4 was also investigated. A StuI recognition site was constructed in the plasmids by localised mutagenesis as described in Example 1. Subsequently the formation of fimbriae and the determination of the antigenicity of these constructs was also determined in the same manner as is described for the constructs of Example 1.

Surprisingly it was discovered that the presence of a mutation in the hypervariable region 1, i.e. the presence of a StuI recognition site, gave recombinant DNA that resulted in the same amount of fimbriae formation by transformed cells as plasmids pAI 410, pAI 430 and pAI 440. The results are given in Table 2.

Construction of the StuI site in hypervariable region 1 seemed to improve the exposure of linkers incorporated in hypervariable region 4. The mutants containing a StuI site in hypervariable region 1 showed a positive reaction in an immuno gold labelling experiment where no label could be detected on cells harbouring plasmid pAI 410 in the same experiment. This finding indicated that the two hypervariable regions under investigation may be in close contact.

EXAMPLE 3

Experiments were carried out with fimbriae preparations comprising recombinant fimbrial filaments obtained from microorganisms transformed with the constructs described in Examples 1 and 2.

Immunisation tests were carried out to determine the neutralising effect on GnRH. The immunisation tests led to the oestrous cycle of the immunised mammal being disturbed or even suppressed.

In this Example mutant fimbriae carrying the amino acid sequence of GnRH were used for vaccination of female rats. The tests were used to ascertain any differences in activity between fimbriae in which only the GnRH-like peptide was constructed in Hypervariable Region 4, HR4 and fimbriae in which in addition another, but very small, change was performed (insertion of a Stu I site in HR1).

After selecting the adult female rats bred from an initial Wistar strain for a regular oestrous cycle they were treated subcutaneously twice, 6 weeks apart, with 0.5 ml of an emulsion of fimbriae (50 μg) in an oil/water mixture (70/30, v/v) of which the oily phase contains Polysorbate 80 and Sorbitan mono-oleate in liquid paraffin (Marcol 52) and the water phase contains $Al(OH)_3$ in distilled water. The mutant fimbriae were pAI 10410, pAI 440 and pAI 10440. The fimbriae-preparations were obtained as described in Examples 1 and 2. Before, between and after the injections daily vaginal smears were taken and at predetermined times blood was collected from the retro-orbital plexus and the sera were stored at −20° C. until assayed. At the end of the experiment the animals were killed and the ovaries weighed.

Vaginal Smears

Daily vaginal smears were made on microscope slides. After drying and fixing with methanol, they were stained for 20 min. with Giemsa solution (Merck, Darmstadt, W. Germany) diluted 1:10 with distilled water, washed thoroughly with tap-water and dried. Each smear was evaluated microscopically (100×) by estimating the percentage of cornified and nucleated epithelial cells and of leucocytes.

The vaginal sequence of normal rats with a 4-day oestrous cycle is:

di-oestrus—pro-oestrus—oestrus. In the figures these oestrous phases are represented by scores:

1=di-oestrus, 2=pro-oestrus and 3=oestrus.

Assay

Binding of $^{125}$I-GnRH by anti-GnRH antibodies in the serum samples was determined by a radioimmunoassay (RIA).

Before incubation the thawed serum samples were diluted in assay buffer ($Na_2HPO_4.2H_2O$, 0.01 mol/L, NaCl, 0.15 mol/L, 0.1% gelatin and 0.1% sodium azide pH 8.0).

The RIA was performed by incubation of duplicates of 0.1 mL diluted serum samples, 0.2 mL assay buffer and 0.05 mL of $^{125}$I-GnRH for 16 hours at 4° C. Prior to the separation 0.05 mL human serum was added to the tubes as carrier protein.

Separation of free and bound was achieved by adding 0.5 mL Peg solution (40% Peg-4000 in assay buffer without gelatin) to all tubes. The mixtures were centrifuged and the precipitate was counted in a gamma-spectrometer.

The titer was calculated as the relative percentage of radioactivity bound as corrected for non-specific binding vs total amount of radioactivity added.

RESULTS

Figure 4:
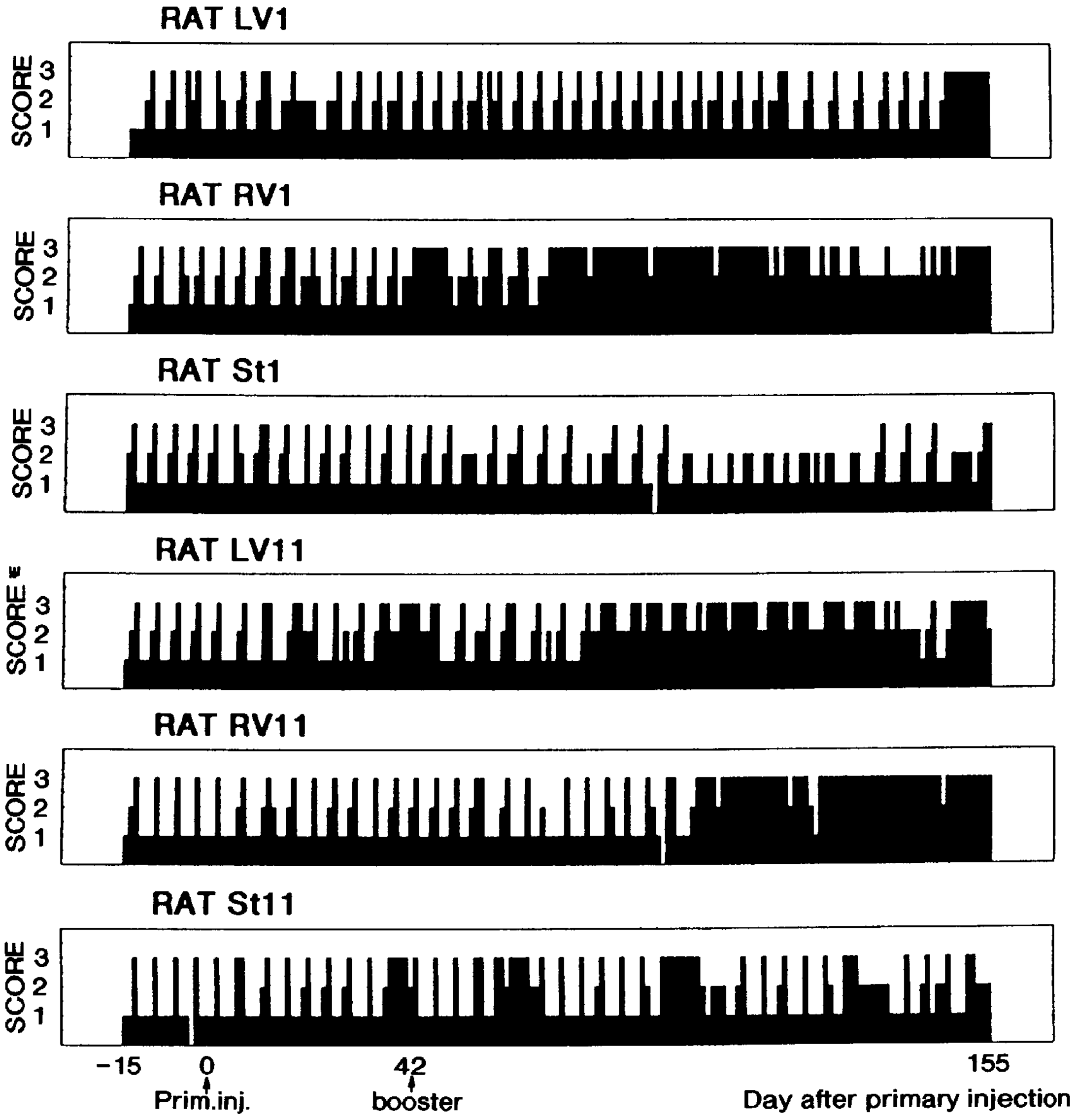
Figure 5:
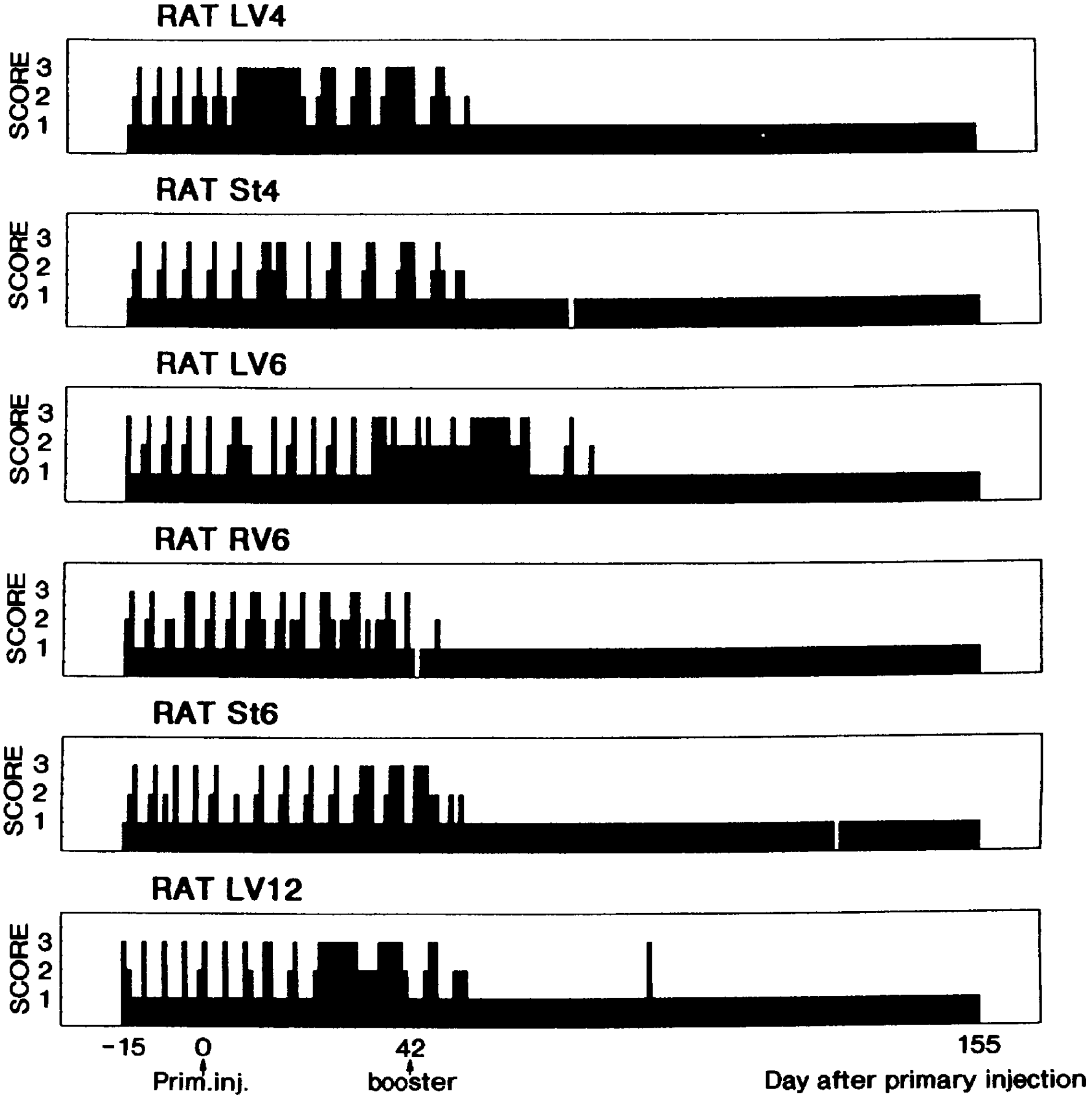

Effects on Anti-GnRH Antibodies and Oestrous Cycle (FIG. 3–5)

- Serum of animals treated with adjuvant only did not show Anti-GnRH antibodies. No suppression of oestrous cycle was observed in these animals.
- All animals treated with the mutant fimbriae showed serum antibody binding which resulted in disruption and suppression of the oestrous cycles.

Body Weights

Figure 6:
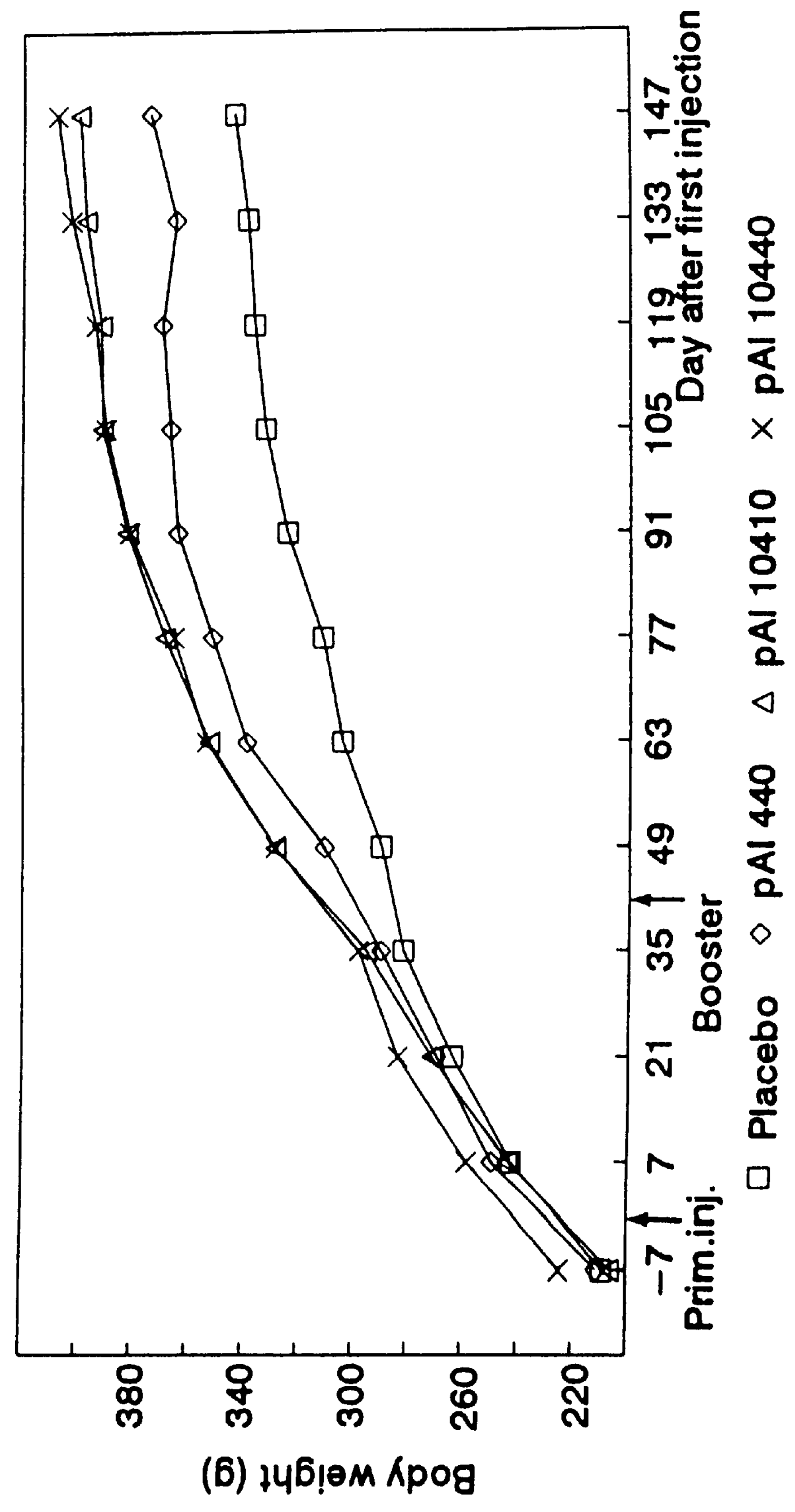

In particular the rats treated with pAI 10410 or pAI 10440 showed higher body weights than the placebo-treated animals from 3–5 weeks after booster injection onwards (FIG. 6).

Ovarian Weights

Figure 7:
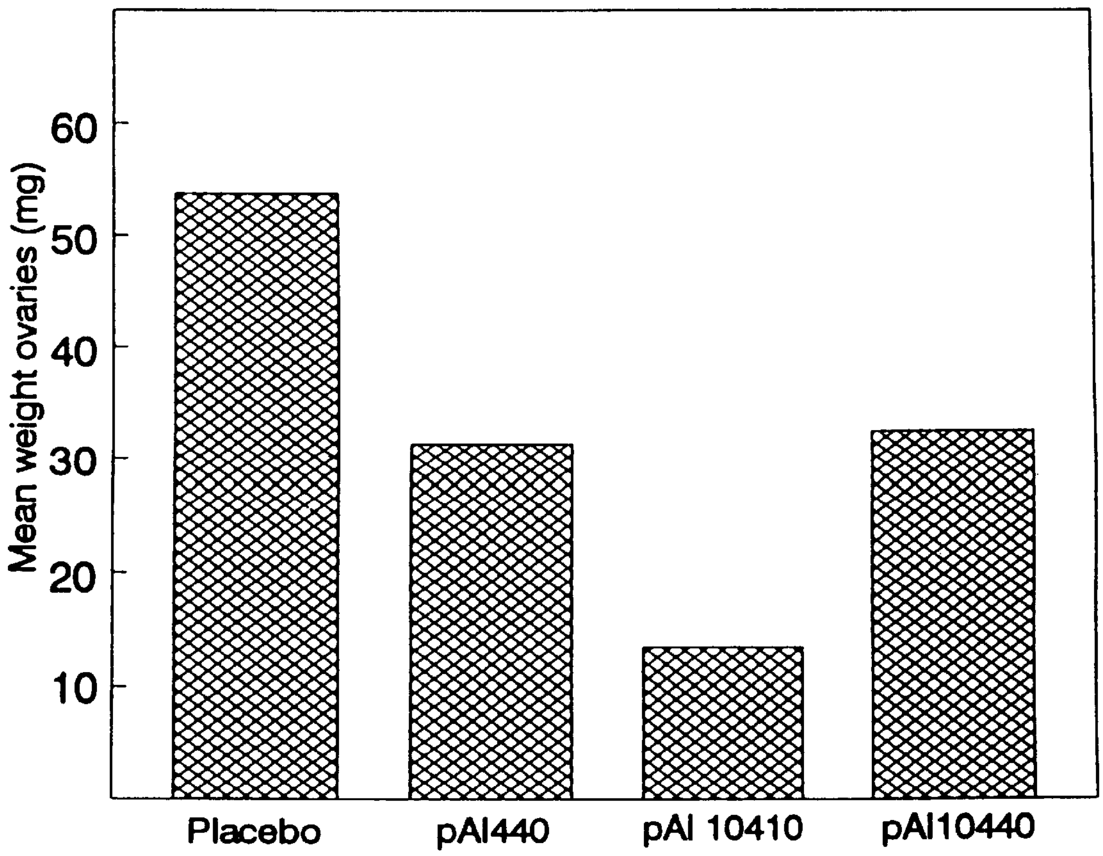

The fimbriae of all mutants caused a reduction in ovarian weight (FIG. 7).

EXAMPLE 4

In addition to the experiment in rats the same preparations were tested in bull calves. Four months old cross bred bull calves were treated subcutaneously twice, 8 weeks apart, with 2 ml of an emulsion of fimbriae (200 $\mu$g) in an oil/water mixture (70/30, v/v) of which the oily phase contains Polysorbate 80 and Sorbitan mono-oleate in liquid paraffin (Marcol 52) and the water phase contains $Al(OH)_3$ in distilled water. The mutant fimbriae were pAI 410, pAI 10410, pAI 440 and pAI 10440. The fimbriae-preparations were obtained as described in Examples 1 and 2. Before, between and after the injections weekly scrotal circumference was determined and at predetermined times blood was collected from the jugular vein and the plasmas were stored at −20° C. until assayed.

Assay

Binding of $^{125}$I-GnRH by anti-GnRH antibodies in the plasma samples was determined by a radio-immunoassay (RIA) as described in Example 3.

Figure 8:
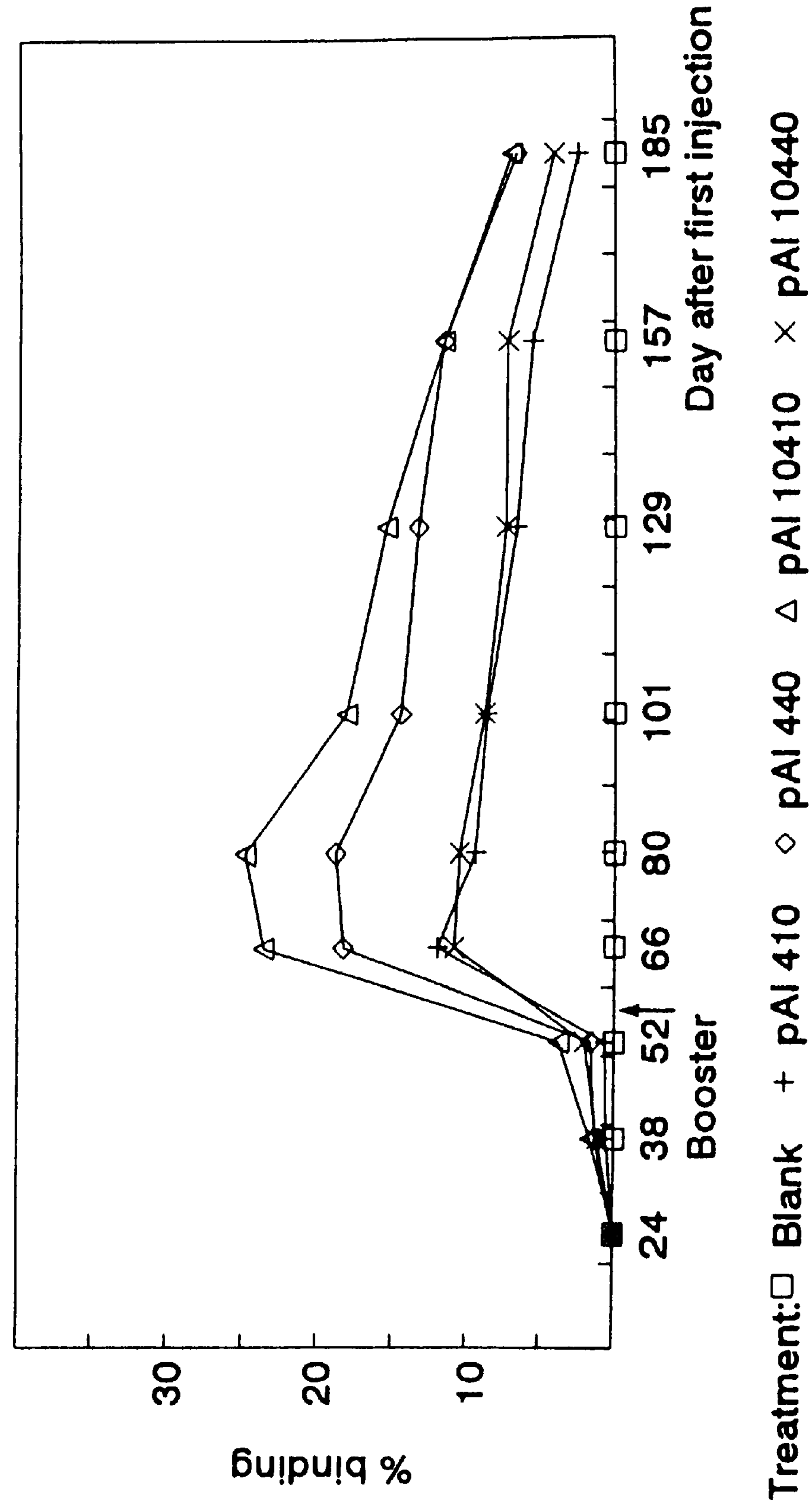
Figure 9:
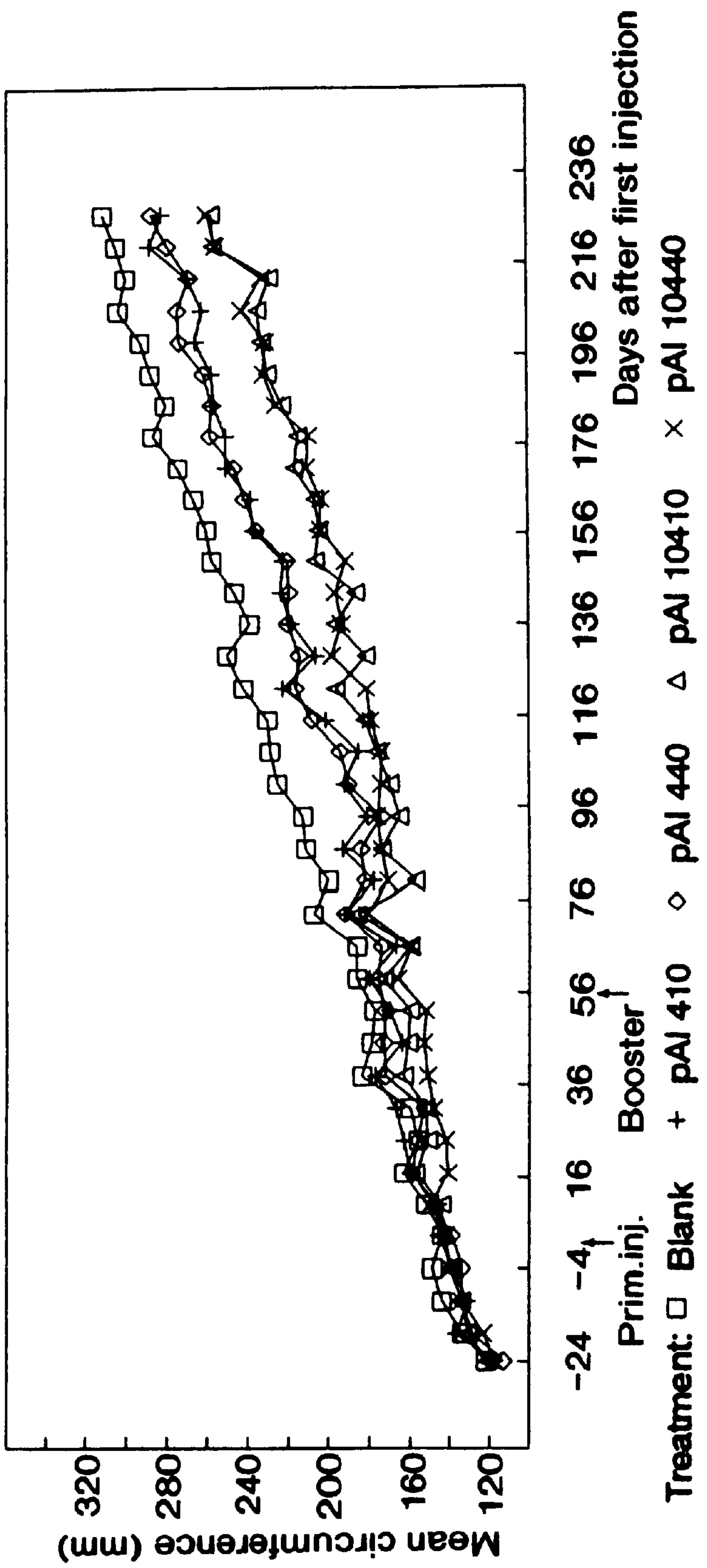

RESULTS (FIG. 8 and 9)

- Plasma of animals treated only with adjuvant did not contain Anti-GnRH antibodies. Scrotal circumference, increased regularly during the experimental period in the four bulls.
- Antibody binding was observed in plasma of bulls treated with pAI 410 which resulted in a reduction in scrotal circumference in comparison to the control animals.
- Antibody binding was observed in plasma of bulls treated with pAI 440 being very high in one animal. This resulted in a reduction in scrotal circumference in comparison to control animals.
- All pAI 10410 treated bulls showed high plasma antibody binding, especially shortly after the booster injection, together with a considerable suppression of scrotal growth in comparison to the control animals.
- The bulls treated with pAI 10440 showed plasma anti-GnRH antibody binding and a considerable reduction in scrotal growth in comparison to the control animals.
- Addition of the Stu1 site in HR 1 resulted in an important improvement of the induction of anti-GnRH antibodies as well as the activity, regardless of whether linker 1 or 4 was used.

TABLE

| linker | HR | length of recombinant HR4 | 5'flanking length | 5'flanking sequence | 3'flanking length | increase in HR4 length |
|---|---|---|---|---|---|---|
| 1 | HR4 | 14 aa | 1 aa | leu | 3 aa | 7 aa |
| 3 | HR4 | 12 aa | 1 aa | leu | 1 aa | 5 aa |
| 4 | HR4 | 15 aa | 2 aa | leu—thr | 3 aa | 8 aa |
| 5 | HR4 | 16 aa | 3 aa | leu—gly—ser | 3 aa | 9 aa |
| wt | — | 7 aa | — | — | — | — |

aa = amino acid
wt = HR4 of original microorganism, no insert

TABLE 2

| | Plasmids | Fimbriation | Insertion site |
|---|---|---|---|
| Hypervariable region 1 | 110 | +/− | HR1 |
| | 130 | ++ | HR1 |
| | 140 | +/− | HR1 |
| | 150 | + | HR1 |
| Hypervariable region 4 | 410 | +++ | HR4 |
| | 430 | +++ | HR4 |
| | 440 | ++++ | HR4 |
| | 450 | +/− | HR4 |
| | 10410 | +++ | HR4 |
| | 10430 | +++ | HR4 |
| | 10440 | +++ | HR4 |
| Wildtype F11 | 291-15 | +++++ | — |

Expression of fimbriae by HB101 cells carrying plasmids encoding the mutant fimbrillins.

TABLE 3

| CONSTRUCT | TITRE |
|---|---|
| pAI 440 | 1:64,000 |
| pAI 440 | 1:32,000 |
| pAI 10410 | 1: 8,000 |
| pAI 10430 | 1:16,000 |
| pAI 10440 | 1:32,000 |
| pPIL291-15 | 1:32,000 |

Results whole-bacteria Elisa on F11 expression.
Bacteria were grown in fermentors in Brain Heart Infusion broth.

Legends

FIG. 1:
Oligonucleotides inserted into plasmids pPIL291-1510 and pPIL291-1519. The encoded GnRH amino acid sequence is underlined.

FIG. 2:
DNA sequences of the recombinant HR4 region in plasmids pAI 410, 430, 440 and 450 and the corresponding amino acid sequences. The encoded GnRH amino acid sequence is underlined.

FIG. 3:
Development of anti-GnRH antibody titers in serum of female rats treated or not with mutant fimbriae carrying the amino acid sequence of GnRH. Relative binding at serum dilution of 5600×.

FIG. 4:
Oestrous cycle of rats treated adjuvant only.

Score: 1=dioestrus
2=pro- or met-oestrus
3=oestrus

FIG. 5:
Oestrus cycle of rats treated with pAI 10410.

Score: 1=dioestrus
2=pro- or met-oestrus
3=oestrus

FIG. 6:
Mean body weights of female rats treated or not with mutant fimbriae carrying the amino acid sequence of GnRH.

FIG. 7:
Ovarian weights of rats treated or not with mutant fimbriae carrying the amino acid sequence of GnRH.

FIG. 8:
Development of anti-GnRH antibody titers in plasma of young calves treated or not with mutant fimbriae carrying the amino sequence of Gonadotropin Releasing Hormone (GnRH). Relative binding at plasma dilution of 5600×.

FIG. 9:
Increase in scrotal circumference in young calves either or not treated with mutant fimbriae carrying the amino acid sequence of GnRH.

We claim:

1. An immunogenic carrier system capable of eliciting an immune response against gonadotropin releasing hormone (GnRH), said carrier system comprising an *E. coli* P-fimbrial filament, which comprises a major subunit with an insert in hypervariable and further comprising a mutation consisting of the creation of a Stu I site in hypervariable region 1, said insert comprising a peptide with an antigenic determinant for GnRH.

2. An immunogenic carrier system according to claim 1, wherein the peptide containing the antigenic determinant for GnRH is derived from the amino acid sequence Gln His Trp Ser Tyr Gly Leu Arg Pro Gly (SEQ ID NO:1).

3. An immunogenic carrier system according to any of the previous claims wherein the major subunit is derived from a P-filament of serotype F-11.

4. An immunogenic carrier system according to any of the previous claims, wherein the insert has a maximum length of 16 amino acids.

5. An immunogenic carrier system according to claim 1, wherein the insert further comprises at least one amino acid flanking the peptide containing the antigenic determinant for GnRH.

6. A vaccine capable of eliciting an immune response against GnRH in an animal, said vaccine comprising an effective amount of an immunogenic carrier system according to claim 1.

* * * * *